United States Patent [19]

Porges

[11] Patent Number: 4,899,101
[45] Date of Patent: Feb. 6, 1990

[54] ONLINE CAPACITIVE DENSITOMETER

[75] Inventor: Karl G. Porges, Evanston, Ill.

[73] Assignee: The United States of America as represented by the United States Department of Energy, Washington, D.C.

[21] Appl. No.: 146,509

[22] Filed: Jan. 21, 1988

[51] Int. Cl.⁴ .......................................... G01R 27/26
[52] U.S. Cl. .................................. 324/663; 73/61 R; 324/71.1
[58] Field of Search .................. 324/61 R, 61 P, 71.1, 324/464, 453, 60 CD; 73/61 R, 861.04

[56] References Cited

U.S. PATENT DOCUMENTS

| | | | |
|---|---|---|---|
| 3,176,222 | 3/1965 | Atkinson | 324/61 P |
| 3,595,078 | 7/1971 | Beck | 73/816.04 |
| 3,635,082 | 1/1972 | Prellwitz et al. | 324/61 R X |
| 3,636,763 | 1/1972 | Beck | 324/61 R X |
| 3,933,030 | 1/1976 | Forster et al. | 324/61 R X |
| 4,011,746 | 3/1977 | Weitz, Jr. et al. | 324/61 R X |
| 4,498,338 | 2/1985 | Peltonen et al. | 324/61 R X |
| 4,633,168 | 12/1986 | Venoma | 324/60 CD |
| 4,713,603 | 12/1987 | Thorn | 324/61 P |
| 4,751,842 | 6/1988 | Ekrann et al. | 324/61 R X |

OTHER PUBLICATIONS

Bobis et al, Particle Velocity and Solid Volume Fraction Measurements With a New Capacitive Flowmeter at the Solid/Gas Flow Test Facility, Aug. 1986, pp. 17–41.

*Primary Examiner*—Reinhard J. Eisenzopf
*Assistant Examiner*—Robert W. Mueller
*Attorney, Agent, or Firm*—Frank J. Kozak; Paul A. Gottlieb; William R. Moser

[57] ABSTRACT

This invention is an apparatus for measuring fluid density of mixed phase fluid flow. The apparatus employs capacitive sensing of the mixed phased flow combined with means for uniformizing the electric field between the capacitor plates to account for flow line geometry. From measurement of fluid density, the solids feedrate can be ascertained.

11 Claims, 7 Drawing Sheets

ONLINE CAPACITIVE DENSITOMETER

CONTRACTUAL ORIGIN OF THE INVENTION

The United States Government has rights in this invention pursuant to Contract No. W-31-109-ENG-38 between the U.S. Department of Energy and the University of Chicago.

BACKGROUND OF THE INVENTION

An online capacitive densitometer has application to the measurement of bulk density and bulk flow of materials conveyed in a mixed phase medium.

Measurement of the density of materials conveyed in a duct or pipeline is needed in a variety of industrial bulk processing operations. In such industrial applications, solid materials in granular or powder form are transported in pipes or ducts by entrainment with a suitable fluid (gas or liquid). The solids may be raw material feedstock or intermediate products of chemical processes which may be run in batch mode or continuous mode. In continuous mode, optimum operation can require accurate control of the material feedrates. This, in turn, requires an accurate on-line measurement of the bulk density of the two-phase medium used to convey the solids.

For single-phase flow, such a measurement is not needed. Instead, the total flowrate can be inferred from an on-line measurement of the duct-averaged flow speed, obtainable by a variety of known and well-tested means. Presence of a second phase complicates measurement because (a) each phase may flow at a different velocity, especially for gas entrainment, (b) the distribution of phases through the duct may be highly inhomogeneous, (c) at desirable measurement sites, such as just before injection into a reactor, elevated temperatures and pressures may prevail, and (d) entrained solids flow constitutes a strongly erosive medium. Therefore, for measurement of a two phase flow, the following conditions apply: (a) At least two variables must be measured, (b) the measurement means should preferably be nonintrusive, and (c) accurate measurement implies accurate averaging over the duct, hence, a sensing device or scheme that senses the duct interior as uniformily as possible. In addition, it is desirable that the instrument can read absolutely and that it feature exceptionally good long-term stability.

Somewhat different specific considerations apply to gas-solid and liquid-solid media. For gas entrainment one typically finds solid volume fractions of less than 0.05, gas velocities of the order of 20 m/s and solid velocities that always have a considerable slip. Solid velocity measurement by cross correlation is readily feasible hence, an additional measurement of the medium bulk density $\rho_m$ or solid volume fractions $\phi_s$ will yield the solid feedrate $m_s$, according to $$m_s = S \, v_s \, \rho_s \, \phi_s \tag{1}$$

where S=duct cross sectional area, $v_s$=solid component velocity, $\rho_s$=intrinsic density of the solid, $\phi_s$=solid volume fraction. The bulk density is given by $$\rho_m = \rho_s \phi_s + \rho_f(1-\phi_s) \tag{2}$$

where $\rho_f$=fluid intrinsic density. Evidently, the second term is very small for a solid-gas medium. Gas entrainment features strongly inhomogeneous solids distributions across the duct, with bottom layers in long horizontal runs and enhanced central solids density elsewhere. Also, the flow regime is invariably highly turbulent.

Liquid-entrained solids conveyors typically feature solid volume fractions in excess of 0.6 which renders the medium highly viscous with a quasi-uniform solids distribution throughout the duct but a flow regime that ranges from transition to laminar/non-Newtonian. Velocity slip is negligible, with a medium velocity typically less than 5 m/s. Here, the bulk density is relatively accurately measurable even if the sensing efficiency is not quite uniform throughout the duct, while the velocity measurement becomes especially difficult.

A densitometer based upon capacitive sensing is ideally suited for making the type of measurement described above. Capacitive sensing is inherently non-invasive and only requires an insulating duct section. An on-line densitometer based on capacitive sensing is a device consisting of a set of electrodes or plates that encompass the medium. An electric field produced between the electrodes by an applied voltage senses the medium dielectric constant which amounts to the ratio of the measured capacity of the device in the presence and in the absence of the medium. Whereas conventional capacity sensors employed for densitometry or moisture measurement usually rely on calibration, there exist some well-established theoretical relations from which a connection can be made between the bulk (medium) dielectric constant and the solid volume fraction. These relations, together with known constants, furnish sufficient data to enable an absolute reading of the solid volume fraction.

In particular, the output signal voltage $e_m$ of an operational amplifier connected to a capacitor whose sensed volume is entirely filled with a two-component medium of the type discussed in the foregoing can be shown to be proportional to the capacity of said capacitor. The same capacitor filled entirely with the pure entraining fluid will yield a slightly different signal voltage, $e_f$. Let the combination $$(e_m - e_f)/e_f = M \tag{3}$$

then, if a fixed capacity $C_s$ exists in series with the capacitor that is filled with the medium, as for example, due to the presence of a dielectric wall between the capacitor plates and the medium, and if $$C_f/C_s = a_s, \tag{4}$$

one readily finds that the quantity M, computed from sample measurements of $e_m$ and $e_f$, equals $$M = (C_m - C_f)/C_f [1 + a_s + a_s(C_m - C_f)/C_f] \tag{5}$$

It is now further well-established based upon the work of Maxwell, Rayleigh, Landauer and Boettcher that the volume fraction $\phi_s$ of the entrained component or solid is related to the quantity $(C_m - C_f)/C_f$ through $$(C_m - C_f)/C_f = B\phi_s/(1 - G\phi_s) \tag{6}$$

where B and G are functions of the dielectric constants of the two phases, fluid and solid. Insofar as these two dielectric constants are known or can be measured, one therefore obtains a direct relation between the sample readout composite M and the solid volume fraction, $$\phi_s = M/(A_0 + A_1 M), \qquad (7)$$

where $$A_0 = B/(1 + a_s),$$

$$A_1 = G - a_s A_0.$$

In turn, the bulk density given by Eq. (2), can be calculated from $\phi_s$ and the known intrinsic densities of the two phases.

It follows that capacitive densitometry can satisfy the requirements specified above, in particular the requirement of absolute readout, through the combination of a capacitive device of suitable geometry and an on-line computer that is programmed to calculate M from sample values of $e_m$ and $e_f$, and to solve Eq. (7) as well as other equations such as Eq. (2), and/or Eq. (1) when the densitometer is deployed in conjunction with a means of measuring the flow speed $v_f$. However, as configured in existing devices, capacitive sensors have not had the capability of uniform sensing throughout the duct, especially with regard to the central concentration of solids that is found in either horizontal or vertical flow.

Other inventions have been directed at improving the accuracy of online densitometers. In U.S. Pat. No. 3,176,222 by E. A. Atkinsson, the invention shows a densitometer having a radial design in which one of the capacitor electrodes is a plug positioned in the interior of the duct by means of mounting struts. The duct wall itself is the other capacitor electrode in this design. The electric field extends radially outward from the plug which is positioned in the center of the duct to the other electrode plate which surrounds it. A disadvantage of this invention is that it requires positioning a plug and mounting struts in the flow thereby subjecting them to abrasive forces of the flow and contributing to the turbulence therein. In U.S. Pat. No. 3,635,082 by Samuel B. Prellwitz, et al., the invention addresses correction of the electric field by means of wrapping narrow electrode plates spirally around and along the duct. The narrow electrode configuration of Prellwitz samples the centerflow more strongly than the peripheral flow, therefore, introducing inaccuracies into the measurement. Furthermore, the narrowness of the plates, and their close proximity to the adjacent plates, results in a relatively weak component of capacity that senses the duct interior, and therefore, a relatively strong parasitic capacity component. This inevitably affects the accuracy of the device.

Furthermore, existing capacitive and other devices intended for online densitometry have not provided an absolute readout but instead, rely on calibration. This can be costly and difficult. For example, when the measurement site features high temperatures and pressures within the duct, then those conditions would have to be reproduced in the test loop or facility where an accurate calibration can be effected. This might require the construction of a special facility. In addition, conventional electronics, even when components of high quality are used, require recalibration as slow changes in gain, phase, supply voltage and frequency are produced by changes in capacity or resistance of circuit elements. The present invention incorporates a specific electronics scheme that, through cancellation of the above mentioned drift effects, achieves a much enhanced long-term stability.

To sum up, the online densitometer will need the following features: First, a capacitor plate geometry design that conforms to a duct of circular cross section (as usually is found in solid/fluid feedlines) yet reads the interior of the duct uniformly without producing field lines that terminate on the signal pickup electrode after passing through the outside surroundings of the duct; second, a strong signal; third, high stability for long intervals; fourth, the capability of producing an absolute measurement so that frequent direct calibration of the instrument is not needed.

It is an object of this invention to secure a highly uniform electric field within an online densitometer.

It is a further object of the invention to provide means that eliminate the possibility of electric field lines of an online densitometer from passing through the surroundings outside the medium.

It is another object of this invention to produce, through the use of online digital computation and exploitation of well-established theoretical equations, an absolute readout.

It is another object of this invention to provide a highly stable electronics scheme that also lends itself readily to online digital computation.

SUMMARY OF THE INVENTION

This invention is an online capacitive densitometer for measuring the solid volume fraction and/or bulk density in two-phase (solid-liquid or solid-gas) media flowing in pipes of circular cross section. This invention includes means for producing highly uniform electric sensing fields within said ducts, thereby providing higher accuracy than has been obtainable with previous inventions. Also included are means for processing electronic analog signals so as to remove the effect of parameter value drifts and thus obtain a highly stable readout, thereby eliminating the need for frequent calibration that characterizes existing capacitive sensing schemes.

Further included is the application of certain theoretical relations, allowing an absolute measurement that needs only a set of constants of the device and of the medium.

This invention is intended to be deployed online in chemical processing plants for the ultimate purpose of feedrate measurement and process control is conjunction with a device or scheme that measures the solids velocity, such as, cross correlation.

BRIEF DESCRIPTION OF THE DRAWINGS

FIG. 2 shows a simplified representation of this embodiment, with electric field lines and equipotential planes drawn in.

DETAILED DESCRIPTION OF THE DRAWINGS

Figure 1:
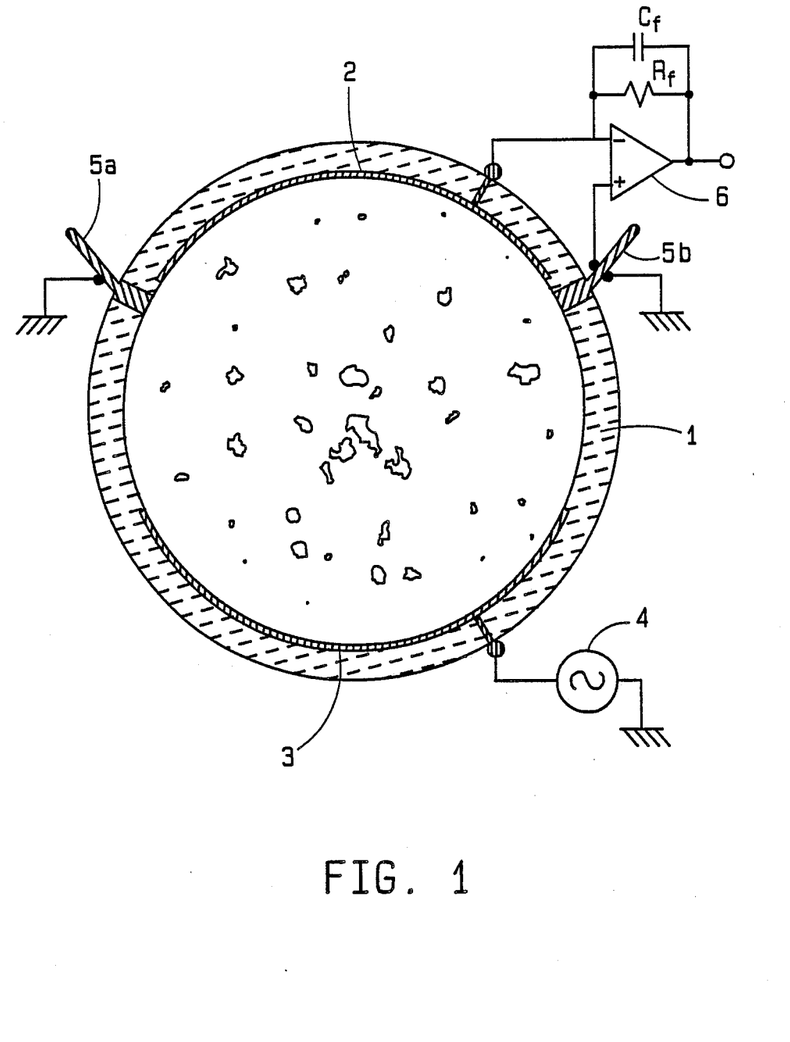
FIG. 1 shows a cross section of one embodiment of this invention, an online capacitive densitometer emplaced on a ceramic or other insulating duct section.

Referring to FIG. 1, there is shown, in cross section, one embodiment of this invention. Duct 1 conveys a mixed phase flow as depicted by the speckled region. Solid granules of varying size and shape are shown entrained by a fluid that may be a liquid or gas. The solid granules typically are distributed non-uniformly across the duct. The duct wall is made from insulating material such as ceramic, glass, or plastic. Embedded flush with the inner wall surface is a set of conductor plates 2 and 3. Alternately, these conductors may be emplaced onto the outer surface of the duct or may form the duct wall itself in circular segments that alternate with insulating segments. These conductors form the electrode plates of a surface-conforming capacitor. In FIG. 1, plate 2 is the signal pickup electrode and plate 3 the driving electrode to which AC potential is applied by means of an oscillator 4, grounded at its other input. Guard strips 5a and 5b are grounded and form a guard/shield structure. The signal pickup electrode plate 2 is connected to the (−) input of operational amplifier 6 with feedback capacitor $C_f$ and feedback resistor $R_f$. For large values of the oscillator frequency, feedback components and series (duct wall) reactances, the readout signal of the amplifier 6 is proportional to the ratio $C_d/C_f$ where $C_d$ =duct capacity. The (+) input of the input stage 6 is grounded hence, the (−) input is effectively grounded.

Figure 2:
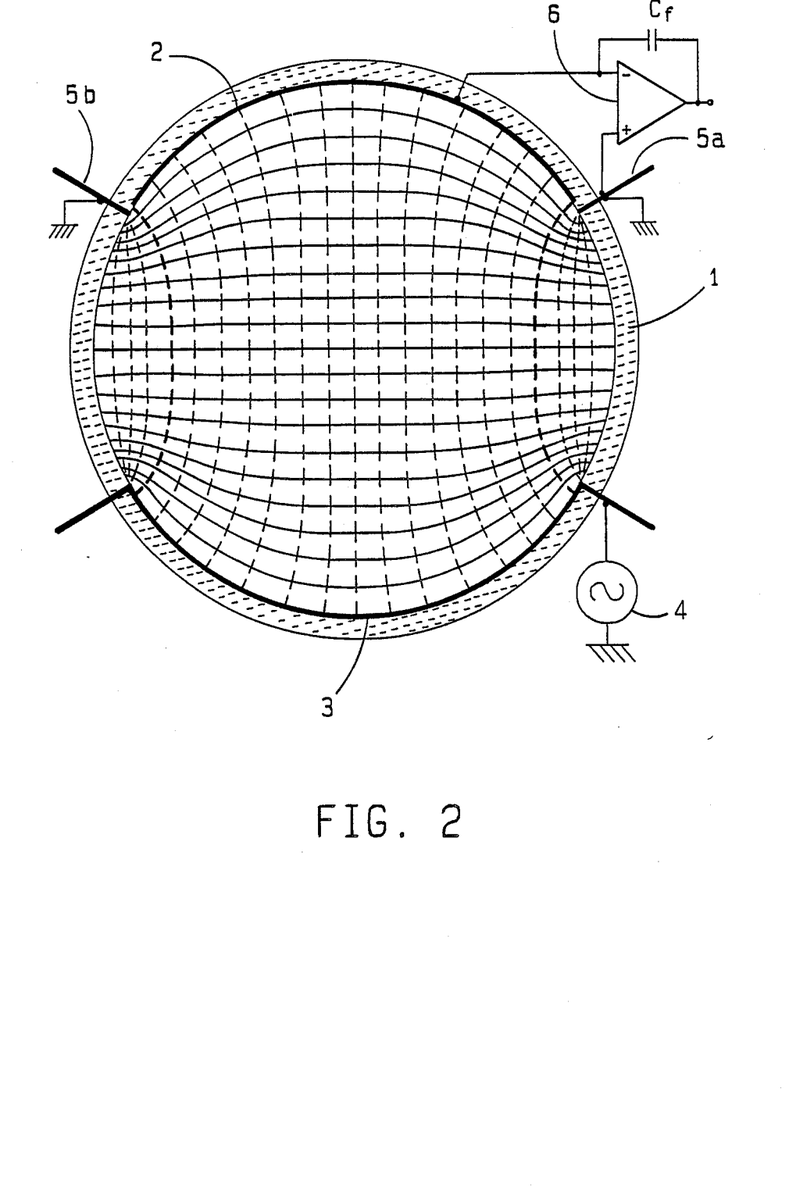
Figure 4:
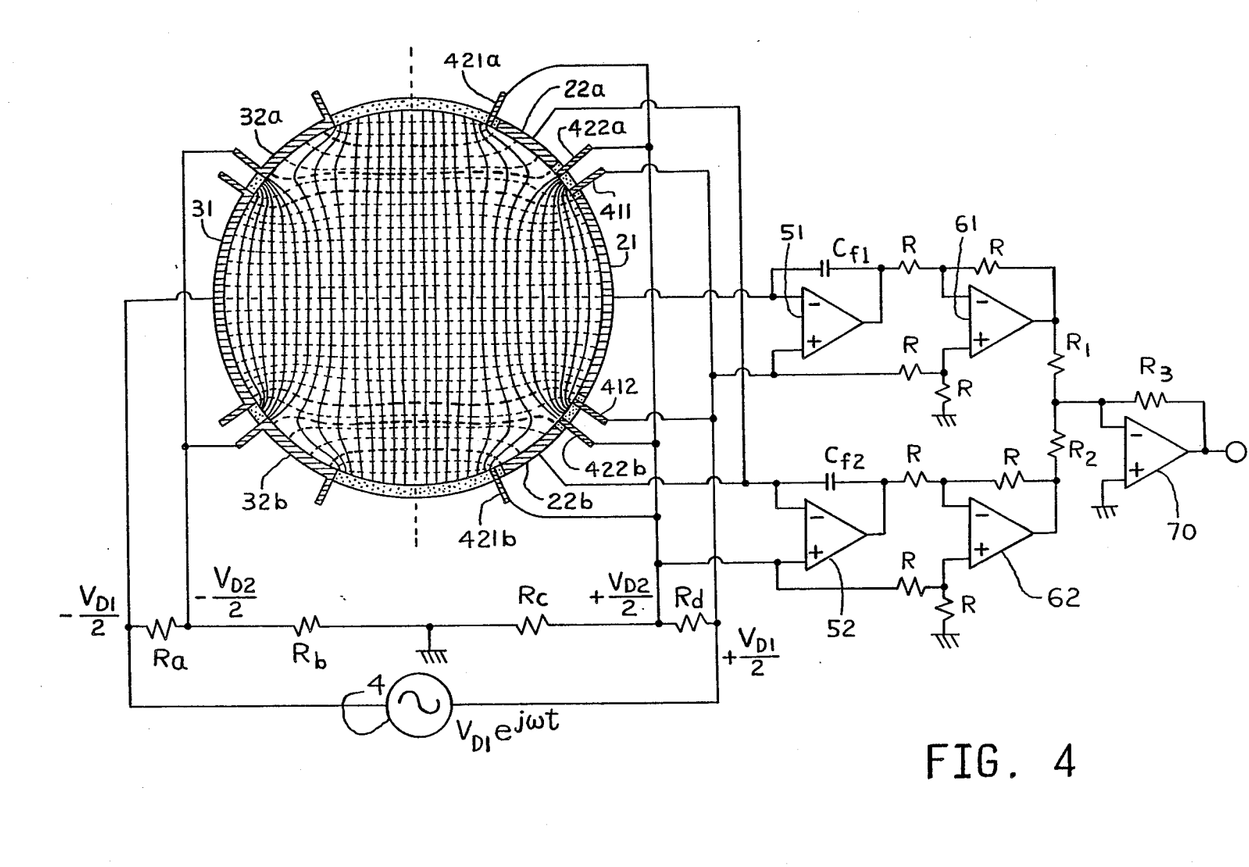
FIG. 4 shows a cross section of another embodiment of this invention.
Figure 5:
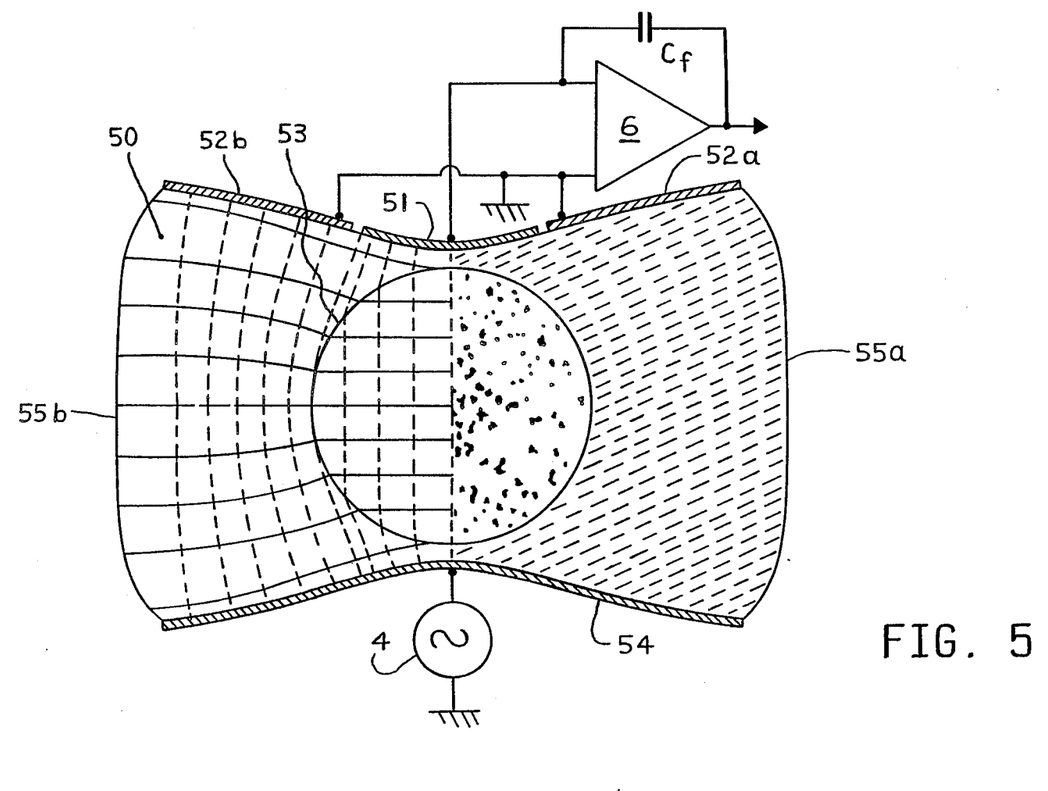
FIG. 5 shows a cross section of still another embodiment of this invention.

Referring to FIG. 2, this depicts the electric field and equipotentials within the region defined by the conforming plate structure. Field lines and equipotentials can be exactly calculated by solving Poisson's equation. Where the field is strong, the equipotentials lie close together. In FIG. 2 and FIGS. 4 and 5, the electric field direction is indicated by broken lines and equipotential by solid lines. Note that the field is a maximum at the plate edge and is close to uniform in the central region between the plates 2 and 3. The region outside the duct bounded by the pickup electrode and guard strips is essentially equipotential, at ground. In the configuration show, the signal pickup electrode plate 2 covers approximately 120 degrees of azimuth, representing a compromise between field uniformity and duct coverage. The sensed part of the duct is indicated by a heavy broken field line that terminates just at the edge of the signal pickup plate. About 92% of the duct cross section is sensed in the configuration shown, and the sensing field is close to uniform within the sensed region.

Figure 3:
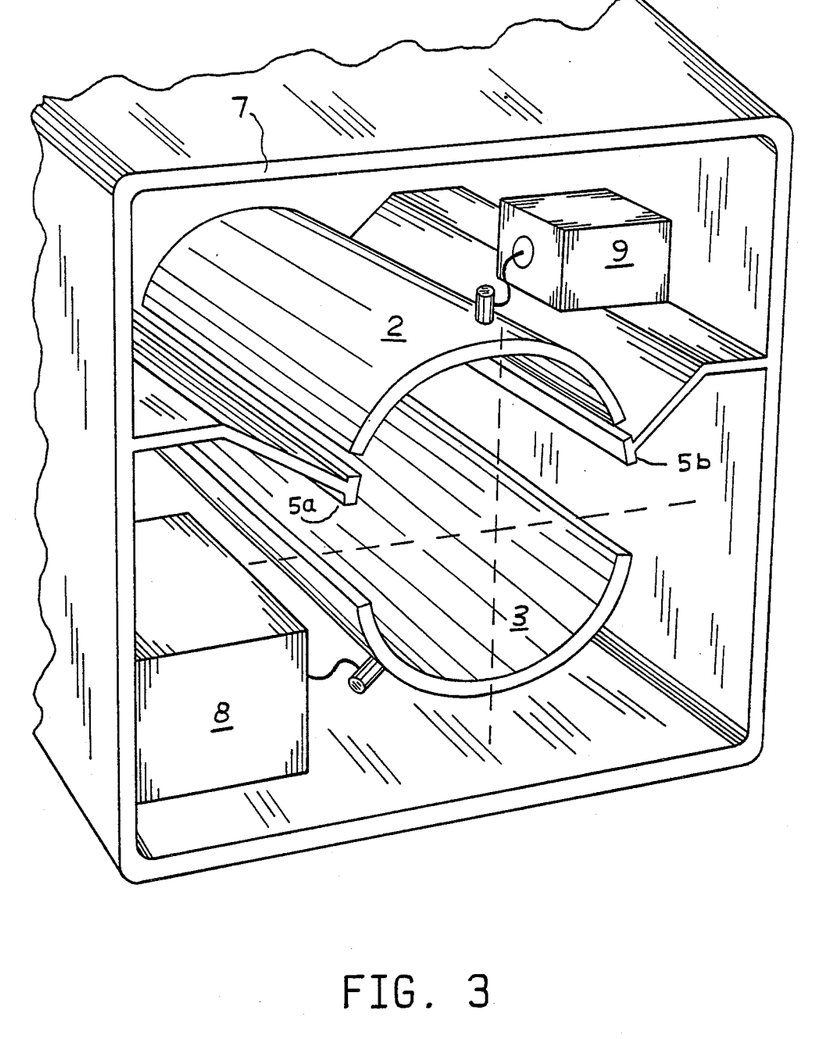
FIGS. 3 shows a perspective view of this embodiment that includes an outer casing; the ceramic duct and some other details are omitted for clarity.

Referring to FIG. 3, this shows a perspective view of the invention as embodied according to FIGS. 1 and 2. Here the ceramic duct has been omitted to allow showing the other features. As indicated, the guard structure can serve to support the ceramic duct section by an extension that is anchored to an outer enclosure wall 7. The enclosure 7 can be employed for electric shielding but can also be equipped with a strongback for relief of mechanical stress on the ceramic.

Within the outer casing of enclosure 7 are shielded boxes 8 and 9 containing the oscillator and input amplifier, respectively. The length of this device along the duct would typically be 20 to 100 cm. Details not shown but normally used, could include: thermal insulation, sensing electrodes that would be deployed in connection with cross correlation flow speed measurement and other devices.

In FIG. 4 is shown another embodiment of this invention. This embodiment is an extension of the previous embodiment and provides for further uniformization of the electric field inside duct 11. It is intended primarily for large ducts. In this embodiment, the capacitor electrode plates are divided into discrete electrically isolated sections 21 and 22a–22b for the signal pickup capacitor electrode plate and 31 and 32a–32b for the driving capacitor electrode plate.

As in the previous embodiment, an oscillator 4 applies an AC potential to driving capacitor electrode plates 31, 32a and 32b. However, the voltage applied to each discrete section is proportional to its mean distance from the other electrode plate. This can be accomplished through a resistive divider $R_a$, $R_b$, $R_c$ and $R_d$. For example, the voltage applied to section 32, $V_{D2}$, is equal to $V_{D1}$ ($d_2/d_1$) where $V_{D1}$ is the voltage applied to section 31, $d_1$ is the mean distance from section 31 to the opposite plate 21, and $d_2$ is the mean distance from section 32 to the opposite plate 22. A similar adjustment is made with respect to the reading capacitor plate sections. This results in a potential distribution that is always symmetrical with respect to the central plane, as indicated in the figure.

Signal pickup plates 21 and 22a–b are each flanked by guard strips 411, 412, 421a, 421b, 422a, and 422b for the reasons already discussed in connection with the previous embodiment. Just as in FIG. 1, the guard strips are at the potentials of the positive ports of the input amplifier 51 and 52. However, the potential divider used in the present configuration places the guard strips at potentials different from ground that need to be subtracted from the capacity signal in second stages 61 and 62; finally the channels must be combined in a stage 70. The particular arrangement shown is only one of several possible configurations. The products $R_1C_{f1}$ and $R_2C_{f2}$ must be chosen to have the ratio $$R_1C_{f1}/R_2C_{f2}=V_{D1}/V_{d2}$$

for an unbiased summing over the entire duct cross section.

As indicated in FIG. 4, the sensing field has been uniformized over most of the duct cross section; the guard strips eliminate those regions where the field still is strongly non-uniform, i.e. in the vicinity of plate edges. For a very large duct, it is possible to further divide the signal pickup plates, producing three or more regions separated by guide strips in a manner analogous to the scheme illustrated in FIG. 4.

In FIG. 5, is shown still a further embodiment of this invention. In the previous embodiment, the measurements of the density was improved by uniformizing the electric field inside the duct by means of dividing the electrode plates into discrete sections. This further embodiment is a practical capacitive sensor geometry that reads the entire duct with an essentially perfectly uniform field, provided that the bulk dielectric constant of the medium does not deviate too much from unity (for which the specific shape of the dielectric applies). As previously noted, the solid volume fraction found in typically pneumatic conveyor lines conveying gas-entrained solids is usually less than 0.05. Therefore, the bulk dielectric constant of these highly dilute media does not deviate much from that of air; i.e. it remains close to unity over the entire practically encountered range of solid concentrations. It follows that the sensing geometry shown in FIG. 5 is applicable for gas-entrained flow on-line measurement, but would not be applicable for liquid-entrained flows where the bulk dielectric constant typically varies over a much larger range while different liquids would call for different capacitor geometries. Practically, the device indicated in FIG. 5 can be fabricated by a number of different means. For example, the dielectric shroud can be build up on the surface of a ceramic tube by mixing a ceramic powder that features a large dielectric constant with resin until the mixture matches the dielectric constant of the tube. This embodiment is particularly suitable for ducts of very modest diameter, where the guard strip design of the previous embodiments would be difficult to implement.

FIG. 5 shows, in cross section, a dielectric shroud 50 with a cylindrical cavity 53 that allows for conveyance of a fluid, depicted as speckles in the right hand side of the figure. The dielectric shroud 50 has concave opposite sides to which conform signal pickup capacitor electrode plate 51, guard electrode plates 52a and 52b and driving capacitor electrode plate 54. Oscillator 4 and amplifier 6 are connected to the electrode plates 51 and 52 as in the previously described embodiments.

As shown in the figure, the opposite concave sides of shroud 50 are shaped so as to conform to equipotential surfaces that can be calculated exactly for the dielectric constant of the shroud material and diameter of duct 53. As shown by the theory of electrostatics, this results in the desired uniform field throughout the cavity. The distances between the lateral cavity walls, and the outer surfaces 55a, 55b of the dielectric must be at least one radius in order to maintain field uniformity within.

With regard to signal processing, Eq. (4) defines the series capacity correction factor $a_s$ that in the case of this embodiment results from the wedge-shaped pieces of dielectric within the sensed region formed by electrode surfaces, the duct wall and the edge of the sensing field (indicated here as elsewhere by a heavy broken line). As stated, the correction factor can be calculated from the known dielectric constant of the shroud, and can be rendered negligibility small by choosing a ceramic with a large dielectric constant.

Figure 6:
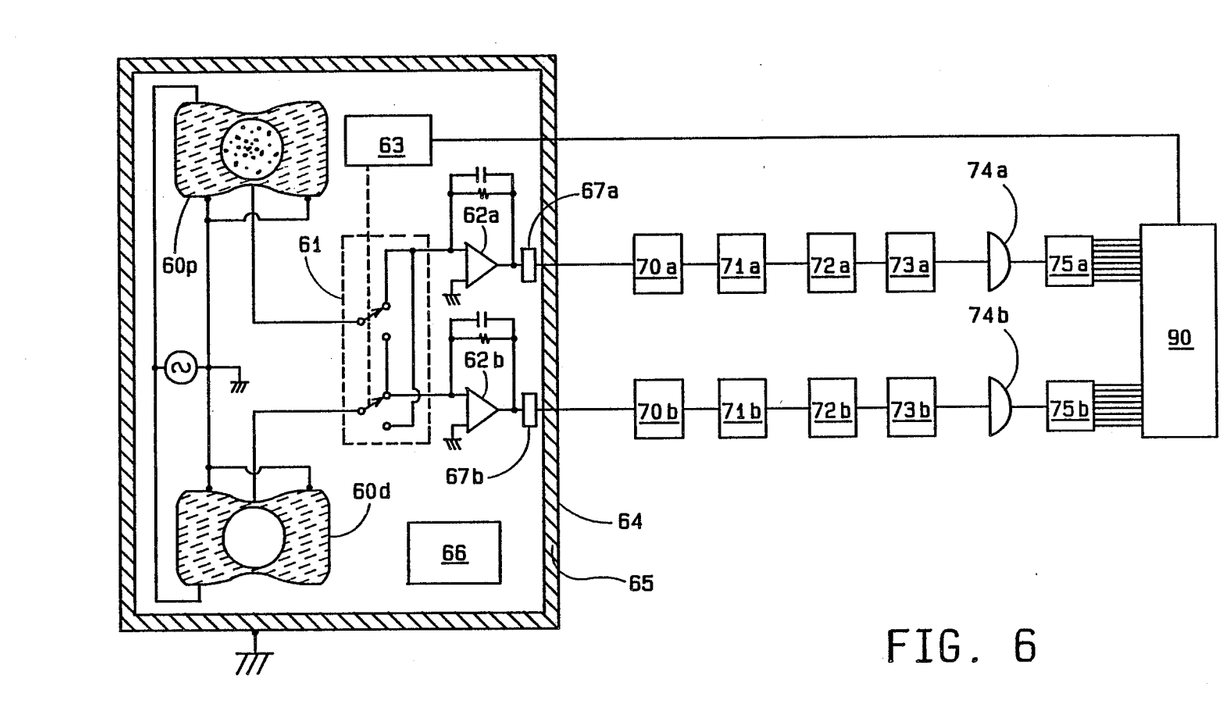
FIG. 6 shows a system diagram that includes a process duct, a dummy duct and electronics devices.

Referring to FIG. 6, there is shown an electronic scheme used in conjunction with a pair of shrouded ducts 60p and 60d, intended to secure an extremely stable readout. Duct 60p is the process duct through which gas-entrained solids pass, while duct 60d is a short dummy duct configured as an exact copy. A means of switching 61 allows alternating connections between 60p and 60d and input amplifiers 62a and 62b. Switching is controlled from an on-line computer through a control device 63. Ducts 60p and 60d and associated electronics are enclosed in a grounded outer casing 64 that also provides mechanical supports. Thermal insulation 65 is provided to keep the capacity of 60p and 60d equal. A temperature sensing and control unit 66 may also be provided. A stable capacitor adjusted to have exactly the capacity $C_f$ of the dummy duct, may be substituted for the latter.

The signals from the process duct 60p and dummy duct 60d are processed through identical parallel electronic circuits "a" and "b" which are alternately switched and sampled to eliminate errors and provide a measurement which does not need to rely on calibration.

The amplifiers 62a and 62b send output signals along identical parallel channels to drivers 67a and 67b which send AC signals through long cables for remote analog processing. Then the signals pass through parallel components which include amplifiers 70a and 70b, demodulators 71a and 71b, filters 72a and 72b and voltage to frequency converters (VFC) 73a and 73b.

The VFC's turn out a train of logic pulses whose frequency varies in proportion to the applied voltage. The VFC pulse trains from the parallel channel outputs of VFC's 73a and 73b are directed to scalers 75a and 75b by a gating system 74a and 74b driven synchronously with the input switching network by computer control. At the end of a given sampling interval of one or several seconds, the gate inhibits further input to the scaler from the VFC, the input amplifiers are switched and the scaler contents are transferred to the computer 90 whereupon the scalers are cleared. After a time of the order of 50 microseconds that allows the analog channel to accommodate to the new average DC level, scaler inputs are enabled and a new set of counts is initiated. Scaler contents represent the time average of the capacitive device signal over the switching (sampling) interval.

Figure 7:
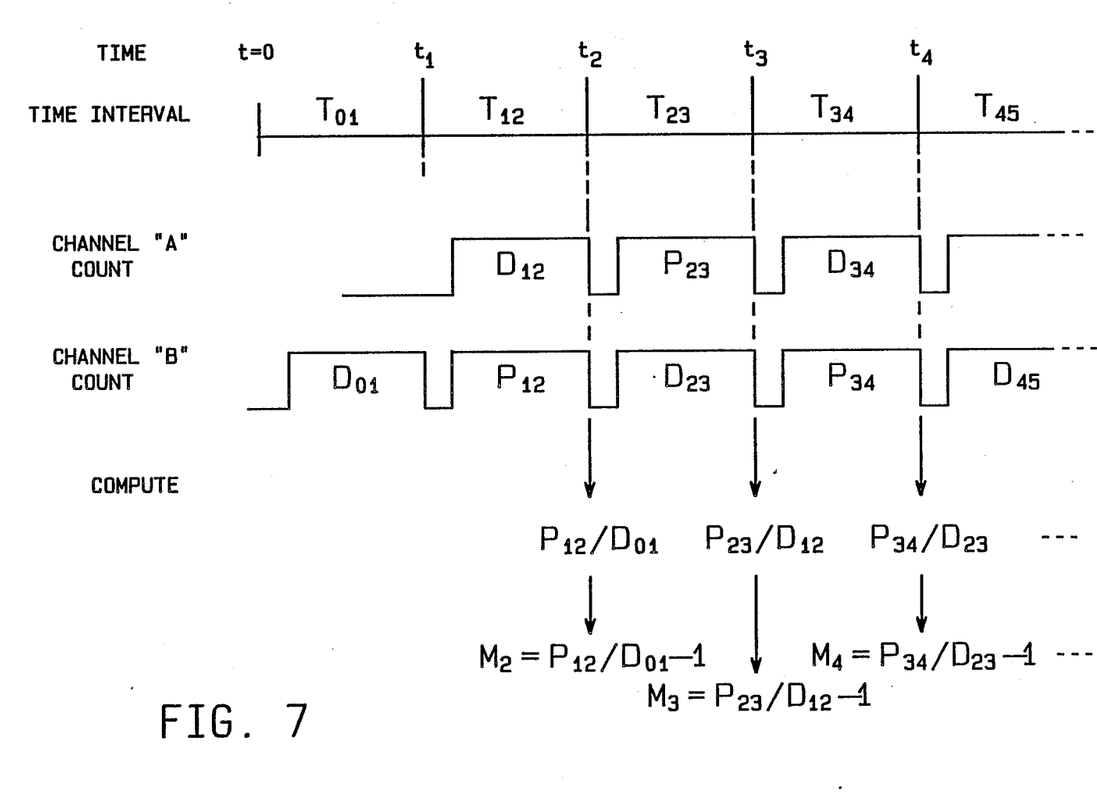

FIG. 7 illustrates the schedule of sample numbers representing the capacity of the process duct and dummy duct, respectively. During time interval $T_{01}$, only the dummy duct is sampled, via its analog channel. During the subsequent internal $T_{12}$, channel "a" processes signals from the dummy duct 60d and channel "b" processes signals from the process duct 60p delivering samples $D_{12}$ and $P_{12}$, respectively. During interval $T_{23}$, channel "a" passes the process duct readout, channel "b", the calculates the ratios $P_{12}/D_{01}$, $P_{23}/D_{12}$, $P_{34}/D_{23}$ etc., thus cancelling all multiplicative factors that vary with channel gain, phase frequency, or component values. The calculation, performed by a Floating Point Coprocessor, makes the response of the instrument considerably more accurate than that of conventional capacitivesensing densitometers that rely on analog computation. In particular, the invention, combining a sensing geometry that offers a very large signal to noise ratio, an analog signal processing scheme of enhanced stability, and digital computation of the result, can measure the density of solids in high dilute, gas-entrained pneumatic conveyors where conventional means of density measurement fail. It further offers an absolute measurement that does not have to rely on calibration.

The embodiments of this invention in which an exclusive property or privilege is claimed are defined as follows:

1. Apparatus for measuring fluid density comprising:
   (a) conveyance means for conveyance of a fluid;
   (b) electrode plates positioned in relation to said conveyance means so that the fluid passes between said electrode plates;
   (c) means for measuring the electrical capacitance of said electrode plates whereby the density of the fluid can be measured;
   (d) means for uniformizing the electrode field between the electrode plates and confining the electric field inside said conveyance means.

2. The apparatus of claim 1 in which the means for uniformizing the electric field between said capacitor plates comprises a guard strip at a fixed reference potential located outside the fluid.

3. The apparatus of claim 2 in which said guard strip extends outward approximately radially from said conveyance means.

4. The apparatus of claim 3 in which the cross-section of said conveyance means is circular and said electrode plates are arcuate conforming in shape to said conveyance means.

5. The apparatus of claim 1 in which said electrode plates are comprised of discrete electrically isolated sections and said means for uniformizing the electric field between the capacitor plate comprises:
   means for applying an electric voltage to each said discrete section of each said electrode plate proportional to the mean distance between that discrete section of said plate and the opposite electrode plate.

6. The apparatus of claim 5 including guard strips at a fixed reference potential located outside of said conveyance means between said electrode plates.

7. The apparatus of claim 6 in which said guard strips extend outward radially from the center of said conveyance means.

8. The apparatus of claim 7 in which the crosssection of said conveyance means is circular and said electrode plates are arcuate conforming in shape to said conveyance means.

9. the apparatus of claim 1 in which the means for uniformizing the electric field between said electrode plates comprises a shroud of material having known dielectric properties and having opposite concave surfaces upon which are proportioned said electrode plates conforming in shape to the concave surfaces.

10. The apparatus of claim 9 in which the opposite concave surfaces of said shroud are shaped so that the electric field generated in said conveyance means by said means for measuring the capacitance is exactly uniform.

11. The apparatus of claim 1 in which the means for measuring the electrical capacitance of said electrode plates comprises:
   (a) a dummy densitometer configured to be similar to said conveyance means, said electrode plates and said means for rectifying the electric field;
   (b) a first signal processing channel;
   (c) a second signal processing channel;
   (d) a switch capable of alternately connecting said electrode plates to said first or said second signal processing channels while at the same time connecting said dummy densitometer to the other signal processing channel;
   (e) voltage to frequency conversion means in each of said channels which comprises means for averaging of the signal voltage through accumulation in a scaler over the switching interval;
   (f) digital processing means to obtain the ratio of process duct capacity to dummy capacity with high accuracy.

* * * * *